United States Patent [19]

Shore

[11] 3,993,161

[45] Nov. 23, 1976

[54] ACOUSTIC HEADSETS

[76] Inventor: Sidney X. Shore, 29 Wren Drive, Roslyn, N.Y. 11576

[22] Filed: Oct. 8, 1975

[21] Appl. No.: 620,633

[52] U.S. Cl. .............................. 181/135; 179/1 ST; 181/131
[51] Int. Cl.² ........................................ A61B 7/02
[58] Field of Search ........................... 181/129–135; 179/1 ST, 156 R, 182 R

[56] References Cited
UNITED STATES PATENTS

| | | | |
|---|---|---|---|
| 3,547,219 | 12/1970 | Bothos | 181/135 |
| 3,730,290 | 5/1973 | Scanlon | 181/135 |
| 3,776,362 | 12/1973 | Rice | 181/135 |
| 3,899,034 | 8/1975 | Stumpf et al. | 181/135 |
| 3,934,674 | 1/1976 | Shore et al. | 181/135 |

*Primary Examiner*—Lawrence R. Franklin

[57] ABSTRACT

The described headsets have earpieces at the ends of acoustic tubing, the tubes being shaped about the wearer's head by a resilient frame that biases the earpieces against the wearer's outer ears. Pairs of spaced-apart strips form resilient arms of the frame and provide inner and outer guides for the acoustic tubes. The inner and outer strips are cross-connected to accommodate flexing of the frame without developing either localized stresses in the strips or significant spreading of the strips when separation of the arms is increased for putting on the headset and while it is worn.

12 Claims, 12 Drawing Figures

U.S. Patent  Nov. 23, 1976  Sheet 1 of 2  3,993,161
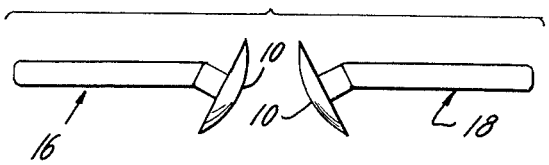
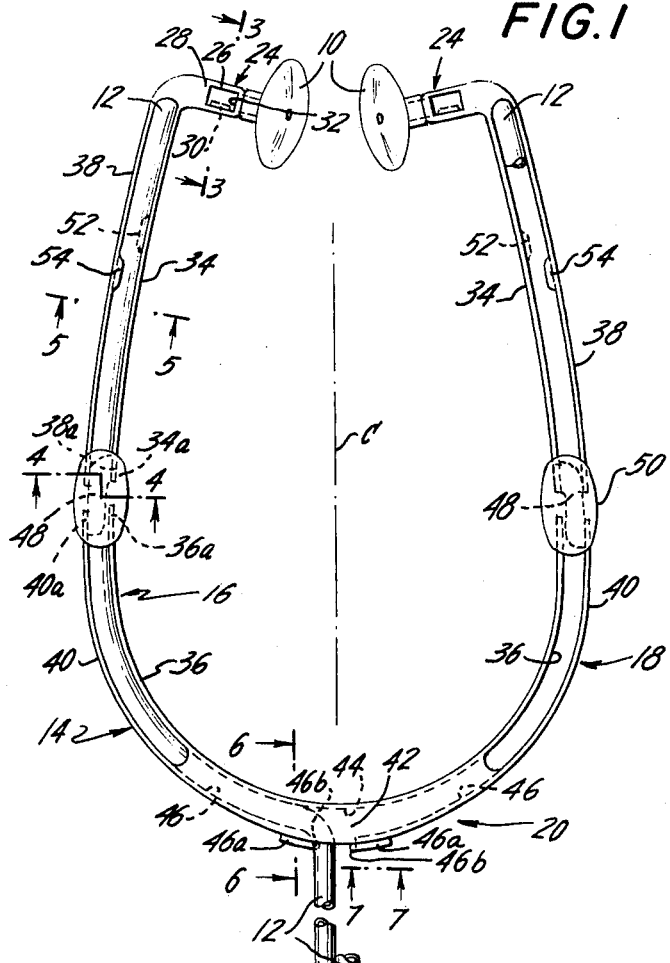
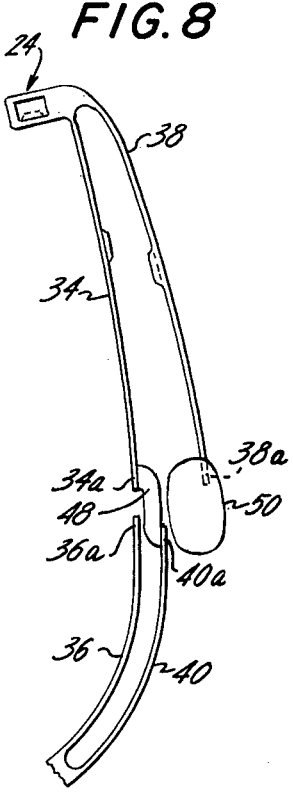
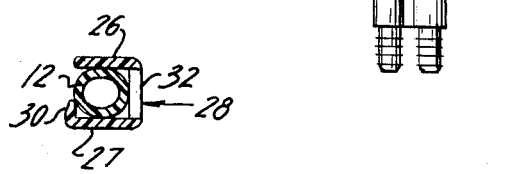
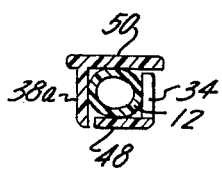
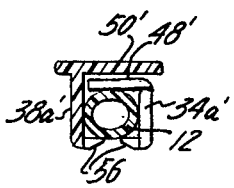
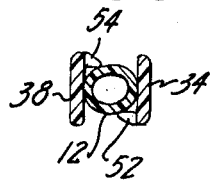
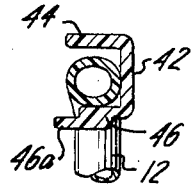
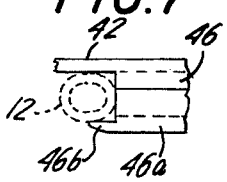

ACOUSTIC HEADSETS

FIELD OF THE INVENTION

This invention relates to frame structures and particularly to acoustic headsets having frame structures that guide acoustic tubes and bias earpieces at the ends of the tubes against a wearer's ears.

BACKGROUND OF THE INVENTION

Acoustic headsets are known having earpieces on the ends of acoustic tubes contained in hingedly connected arms. Such frames tend to be expensive because of costs related to their hinge, and they do not bias the earpieces against the wearer's ears. Similar headsets are known (as in U.S. Pat. No. 2,142,407, issued Jan. 3, 1938 to Norton et al.) wherein a resilient frame has loops containing acoustic tubes. Such a frame cannot be molded, and assembly of the tube into tubular collars of the frame is inherently time-consuming, both of these considerations rendering such construction unduly expensive. Another such headset is disclosed in U.S. Pat. No. 3,730,290, issued May 1, 1973 to Scanlon, wherein acoustic tubes contained in rigid channel-shaped arms are connected by a resilient strip that provides bias to hold the earpieces against a wearer's ears. The frame of that headset can be molded of plastic material, promoting low cost. The design of the frame is intended to direct the earpieces at desired angles toward the wearer's ears. The resilient connecting strip between the rigid arms of that headset unfortunately is poorly adapted to resist stresses that develop in use which may cause the arms to become skewed, the earpieces then becoming misdirected. Moreover, the resilient connecting strip is poorly adapted to resist warping stresses that may occur when the headsets are stored, occasionally resulting in permanently deformed headsets.

Copending application Ser. No. 501,688 filed Aug. 29, 1974 by Sidney X Shore and Paul S. Martin, now U.S. Pat. No. 3,934,674 provides an acoustic headset having a frame for acoustic tubes, where resilience for biasing the earpieces against a wearer's ears is provided partly or wholly by arms of the frame. The Shore et al headset represents an improvement over the prior art, but the illustrative form of that invention involves objections which are discussed below.

SUMMARY OF THE INVENTION

The present invention provides a novel resilient frame, and a novel acoustic headset having features in common with that of Shore et al. mentioned above. The arms of the present frame and the arms of the Shore et al. frame are formed of paired strips that fix the shape of the acoustic tubes extending to the earpieces and direct the earpieces at desired angles toward the wearer's ears. In accordance with the present invention, respective inner and outer strips of the frame are cross-connected to provide compensation for differential changes in length that tend to occur between inner and outer strips when the arms of the frame are being spread apart. In this way the advantages of the illustrative headset of Shore et al. are retained, but its disadvantages are avoided.

The objects of the invention, and the foregoing and other novel features and advantages, will be more fully appreciated from the following detailed description of the presently preferred embodiment and various modifications, and from the accompanying drawings forming part of the disclosure of those embodiments of the invention.

DESCRIPTION OF THE DRAWINGS

FIG. 1 is the front view of an acoustic headset, being the presently preferred embodiment of the invention, portions of the tubing of the headset being broken away;

FIG. 2 is a top plan view of the headset of FIG. 1;

FIGS. 3, 4, 5 and 6 are cross-sections of the headset of FIG. 1 as viewed from the cross-sectional planes 3—3, 4—4, 5—5 and 6—6, respectively, in FIG. 1;

FIGS. 4A and 5A are modifications of FIGS. 4 and 5, respectively;

FIG. 7 is a fragmentary elevation of a portion of the preferred embodiment as viewed from the plane 7—7 in FIG. 1, including an acoustic tube shown in broken lines;

FIG. 8 is a fragmentary view of the frame of FIG. 1, at an intermediate stage of its manufacture;

THE ILLUSTRATIVE EMBODIMENTS

Figure 9:
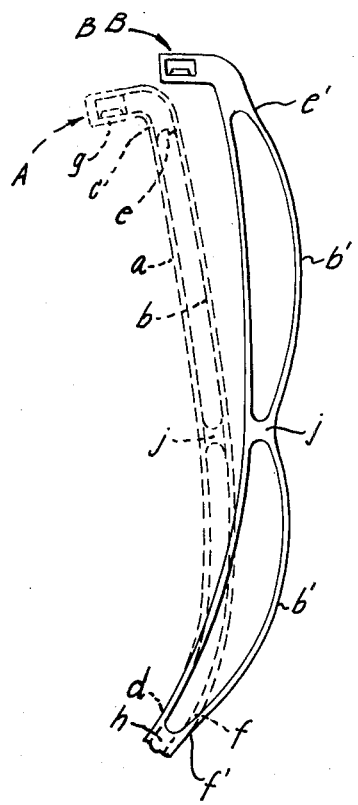
FIG. 9 is a partial view of an arm of the frame in application Ser. No. 501,688 mentioned above, its normal position appearing in broken lines and its stressed position appearing in solid lines, drawn to reduced scale.

Referring now to FIG. 9 of the drawings, a view A of one arm of the frame of application Ser. No. 501,688 is shown in broken lines in its normal unstressed state and a second view B of the same arm is shown with the arm in its stressed condition, as it appears when the arms of the frame are spread apart while being worn. As seen in view A, the arm has inner strip *a* and outer strip *b* whose extremities *c*, *d*, *e* and *f* are united to in-turned end portion *g* and medial portion *h* of the frame. A bridge *j* connects strips *a* and *b* between their extremities. The arm in view A contains an acoustic tube (not shown) between strips *a* and *b* which are equally spaced along their lengths in condition A.

In position B of the arm, strip *b* forms bulges *b'* above and below bridge *j*, illustrating an increase in the separation between strips *a* and *b*. First, these bulges impair the appearance of the frame. Second, high stresses develop at the extremities of outer strip *b* at points *e'* and *f'* and where strip *b* is united to bridge *j*. Additionally, there is some loss of constraint of the acoustic tube (not shown) between strips *a* and *b*, so that the acoustic tube might sag partly outside the space between the strips. These bulges and stress points of strip *b* are largely or entirely avoided in the frames of FIGS. 1 and 10.

In FIG. 1 earpieces 10 are carried on the upper ends of acoustic tubes 12. Parts of the total length of those tubes extending from earpieces 10 are constrained by frame 14 into position about the wearer's face. This frame can be manufactured economically by molding it in one piece of a suitable thermoplastic. Resilient arms 16 and 18 of the generally U-shaped frame are connected by rigid medial portion 20. Tubes 12 extend to a plug 22 to be inserted into a two-channel stereo sound outlet commonly available in passenger airplanes.

The tubes 12 contained in arms 16 and 18 are of essentially limp plastic but inherently they have some minimal stiffness. Arms 16 and 18 are prominently resilient. They develop sufficient bias to assure earpieces 10 being pressed against the outer ears of the wearer. The pressure is to be held to a minimum, to avoid causing pain that can develop over a long wearing period.

While the frame develops only light pressure, it is not frail. The illustrated frame is quite sturdy and is well suited to resist deformation during handling and storage. This is important in order for the earpieces to be directed at desired angles (see FIG. 2) toward the wearer's ear canals.

Arms 16 and 18 include respective in-turned portions 24. As seen in FIG. 3, the cross-section of each in-turned end portion 24 is essentially channel-shaped, including side walls 26 and 27 and "bottom" 28 of the channel. Tube 12 is retained in the channel by detent 30 forming a constriction at the nominally open side or "top" of the channel, opposite bottom 28, which is the closed side of the channel (disregarding opening 32). Opening 32 in the bottom of the channel facilitates molding of detent 30.

The U shape of frame 14 is symmetrical about imaginary center line C. Each of the arms 16 and 18 consists largely of pairs of opposed strips, separated from each other along most of their length by the diameter of tube 12. The strips include "inner" and "outer" strips, respectively closer to and farther from centerline C as a reference. However, when the arms of the frame are spread apart for putting the headset on the wearer, the separation of the strips remains nearly if not precisely constant. The bulges k in FIG. 9 are avoided, despite the fact that each flexible arm of the frame undergoes a change of shape enough to (ordinarily) require stretching of the inner strips and/or shortening of the outer strips. The material of the frame (such as polypropylene) is resilient but it is not an elastomer or a plastomer so tht it cannot stretch or become shortened to accommodate such changes.

Each arm 16 and 18 includes two inner strips 34 and 36, which are serially aligned with each other along the arm or are at least approximately endwise opposite one another to be mechanically in series; and each arm 16 and 18 also includes two outer strips 38 and 40 that are serially aligned with each other or are mechanically in series. The width of these strips is approximately the same as the diameter of tubes 12, although strips 36 and 40 may be made progressively still wider toward their lower ends as a matter of design. The upper extremities of strips 34 and 38 are fixed to and are unitary extensions of in-turned end portions 24 of the frame. Medial portion 20 of the frame is roughly channel-shaped, the bottom of the channel 42 forming a front portion of the frame and the sides 44 and 46 of the channel forming extensions of strips 36 and 40. Strips 36 and 40 are unitary, integral extensions of walls 44 and 46 of the channel. An off-set portion 46a (FIGS. 1 and 6) of each channel wall 46 carries a hook 46b (FIG. 7). Hooks 46b cooperate with the opposite bottom wall 42 and the opposite ends of walls 46 to grip and securely retain the pair of tubes 12 where the tubes emerge from the frame. Portions 46a are off-set from channel walls 46 to enable molding of hooks 46b without resort to a complicated and costly mold construction.

A cross-connector 48 unites the lower end portion 34a of inner strip 34 and the upper end portion 40a of outer strip 40, these parts being molded as unitary parts of the frame. Cross-connector 50 unites the lower end portion 38a of outer strip 38 to the upper end portion 36a of inner strip 36. Cross-connectors 48 and 50 are at the back and front, respectively, of frame 14 (FIG. 4) so as to surround acoustic tube 12 and they are spaced apart by the diameter of the tube. There is preferably some little clearance between the frame and tube 12 at this region, or the tube may be tightly received, but in any event, the tube and each of the cross-connectors are movable in relation to each other along tube 12.

As indicated above, the entire frame is molded of one piece in the illustrated embodiment. It is considered that cross-connectors 50 may be made as separate pieces and then united by supersonic welding, gluing or tightly fitted mechanical joints to strip end-portions 36a and 38a. However (FIG. 8) cross-connector 50 is here molded integrally with strip 38 at its lower end portion 38. Cross-connector 50 and strip 38 are shown in FIG. 8 as the frame is molded, shifted away from the rest of the frame to enable the entire frame to be molded of one piece using a simple molding die. Thereafter, preferably following assembly of tubes 12 into the frame, cross-connector 50 of each arm is shifted into position opposite the upper end portion 36a of strip 36 and then united to that strip as by supersonic welding, by cement or by mechanically interlocking formations on cross-connector 50 and strip end portion 36a.

Cross-connector 50 is shown wider than the rest of the arm defined by strips 34, 36, 38 and 40, to provide space for decoration such as a decorative trademark. Alternatively, cross-connector 50 may be made narrower, so as to conform to the contour of the strips. Where cross-connector 50 is made as a separate piece, it may be formed of a differently colored material for decorative purpose, but the cost of the frame would be higher than molding the frame of one piece as shown in FIG. 8.

As seen in FIG. 4, cross-connector 48 is formed along the plane of the back edge of strip 34, to accommodate and contain the full cross-section of tube 12. By making lower end portion 38a wider than strip 34 and wider than the rest of strip 38, it can serve as a stop when cross-connector 50 is displaced from its position in FIG. 8 to that in FIG. 1.

Tubes 12 tend to remain in position between the paired strips forming arms 16 and 18, by virtue of detention in in-turned portion 24 and between cross-connectors 48 and 50 and due to confinement in medial portion 20 of the frame. However, if desired, detent 52 at the back edge of strip 34 (FIGS. 1 and 5) and detent 54 at the front edge of strip 38 may be included. The detents need not be prominent to be effective, inasmuch as the space between strips 34 and 38 tends to stay the same when arms 16 and 18 are manipulated for putting on and taking off the headset. As a further alternative, the detents may be elongated so as to extend along the whole length of their respective arms, such elongated "detent" 52' (FIG. 5A) being disposed behind tube 12 and such extended detent 54' being disposed in front of the tube 12, for positive guidance of the tube all along the arms.

The frame 14 is molded with arms 16 and 18 closer together than in their usual flexed or stressed relationship when the headset is worn. The resilience of arms (as determined largely by the cross-section of the strips forming the arm and the material used) provides gentle bias of the earpieces 10 against the wearer, and yet the arms can be spread relatively widely in putting the headset on or taking it off, and when worn by people having either small or large heads.

During flexing of the arms as they are being spread apart, all of the strips undergo a change in curvature. Outer strips 38 and 40 are stressed in a sense tending to cause them to become compressed, while the stress in strips 34 and 36 tends to cause elongation. By virtue of outer strip 38 being connected to inner strip 36 and outer strip 40 being connected to inner strip 34, the tendencies of the stresses to produce elongations and compressions of the inner and outer strips does not cause bulges to form as in the frame of FIG. 9, and localized stresses related to the construction of FIG. 9 are avoided in the frame of FIG. 1. Moreover, the space between the inner and outer strips remains virtually constant so that the appearance of the frame is not harmed such as would result from a change in strip-to-strip spacing during manipulation, and where detents 52 and 54 are used, they remain effective during manipulation of the frame.

During outward flexing of the arms, the adjacent end portions 38a and 40a of the outer strips tend to move closer together. Consequently, some space is provided between those end portions in the unstressed condition of the frame.

Strips 36 and 40 are shown a bit shorter than strips 34 and 38. This proportion is empirically selected to take into account the respective changes in length of the strips needed to accommodate flexing of the arms. There is inherently a greater effect produced on the strips farther from end portions 24 of the frame than occurs in the portions of the strips nearer those end portions, because the separating force is applied at the ends of the arms. Consequently optimum design depends on many factors, such as whether all the strips are of uniform width and thickness or whether (see above) there is progressive increase in strip width toward medial portion 20 of the frame.

Despite the relatively light resilient bias of the earpieces developed by the frame during spreading of the arms, the frame is remarkably stable in its shape in other respects. It resists twisting of the arms, such as might disturb the direction of the earpieces at the desired angles toward the wearer's ears. Twisting stresses may develop in some forms of frame both during storage (which might well cause permanent warping of the frame) and during use, but the illustrated construction is well adapted to resist such stresses.

FIG. 4A illustrates a modified detail. Parts in FIG. 4A are given primed numerals corresponding to the parts of FIGS. 1 and 4, and the description of the basic construction is not repeated. The main difference is that cross-connector 48' in FIG. 4A is at the front of the frame directly under cross-connector 50'. This arrangement makes assembly of the headset somewhat easier. Fabrication of the frame can be completed at first and then the tubes 12 can be pressed into place. Detents 56 at the back edges of strips 34 and 38 near cross-connectors 48' and 50' can then be added, if required, to retain tubes 12 in position between the strips.

Figure 10:
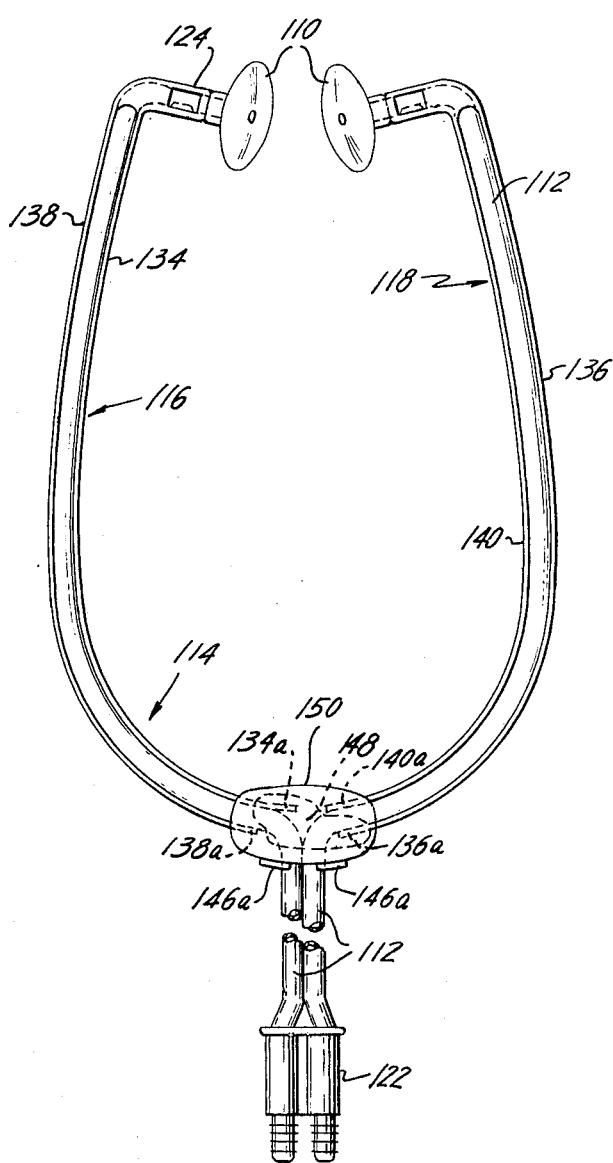
FIG. 10 is a front elevation of another embodiment of features of the present invention.

A modification is shown in FIG. 10, where 100-series numbers are used for parts corresponding roughly to parts in FIG. 1. Earpieces 110 are biased toward the ears of a wearer by the modified frame 114 containing acoustic tubes 112. Arm 116 conists of inner and outer strips 134 and 138, and arm 118 consists largely of inner and outer strips 140 and 136, respectively. Cross-connector 148 unites end portion 134a of inner strip 134 and end portion 136a of outer strip 136. Correspondingly cross-connector 150 unites the end portion 138a of outer strip 138 and end portion 140a of inner strip 140. The cross-sections of these strips is in accordance with either that in FIG. 4 or that illustrated in FIG. 4A. Detents (not shown, such as detents 52 and 54 or detents 52' and 54') should be distributed along the strips. Cross-connector 150 bears integral tube retainers 146a like retainers 46a and 46b of FIGS. 1, 6 and 7. In use, the lengths of inner and outer strips of arm 116 tend to become differentially changed, but that effect is accommodated by the inverse effects in the cross-connected outer and inner strips of arms 116 and 118. It will be understood that other details in the frame of FIG. 1 are applicable in frame 114 of FIG. 10, but are not repeated here.

What is claimed is:

1. An acoustic headset including a pair of earpieces, a pair of acoustic tubes having respective first tube ends bearing said earpieces and means remote from said first tube ends for coupling said tubes to sound-source means, and a resilient frame, said frame including resilient spaced-apart arms having end portions supporting said first ends of said tubes for directing and biasing said earpieces toward the ear canals of a wearer, said arms being united to each other and being formed largely of opposed but spaced-apart inner and outer strips, said inner strips being disposed closer to a centerline between the spaced-apart arms than said outer strips and each of said tubes having lengths thereof disposed in the space between said opposed inner and outer strips, said strips including first and second inner strips disposed in series and having respective first and second end portions adjacent each other and said strips including third and fourth outer strips disposed in series and opposed to said first and second strips respectively and having respective third and fourth end portions adjacent each other, a first cross-connector uniting said first and fourth end portions and a second cross-connector uniting said second and third end portions of said strips, said cross-connectors forming the sole connections between said strips in the region of said first, second, third and fourth end portions of the strips.

2. An acoustic headset in accordance with claim 1, wherein said frame further includes a medial portion bearing said arms and wherein each of said arms includes first, second, third and fourth strips and first and second cross-connectors all as aforesaid between said medial portion and the earpiece supporting end portion of the arm.

3. An acoustic headset in accordance with claim 2, wherein said first and third strips extend from said end portions of said frame and are appreciably longer than said second and fourth strips for enabling the space between the opposed strips to remain virtually constant despite the greater stress inherently imposed on said second and fourth strips than on said first and third strips when the end portions of the frame are pulled farther apart than in the unstressed condition of the frame.

4. An acoustic headset in accordance with claim 2, wherein said first and second cross-connectors of each of said arms are disposed at opposite sides of said tubes, respectively.

5. An acoustic headset in accordance with claim 1, wherein one of said arms is formed largely of said first and third strips and the other of said arms is formed of said second and fourth strips.

6. An acoustic headset in accordance with claim 1, wherein said inner strips are in endwise alignment and wherein said outer strips are in endwise alignment and said third and fourth end portions thereof are spaced apart in the unstressed condition of the frame so that they are free to move closer together as the end portions of the arms are being spread apart.

7. A resilient frame having end portions connected to resilient arms for supporting earpieces and directing the earpieces toward the ears of a wearer, said arms being formed largely of inner and outer pairs of opposed strips, said inner strips being disposed closer to a centerline between the spaced-apart arms than said outer strips, said strips including first and second inner strips disposed in series and having respective first and second end portions adjacent each other and said strips including third and fourth outer strps disposed in series and opposed to said first and second strips, respectively, and having respective third and fourth end portions adjacent each other, a first cross-connector uniting said first and fourth end portions of said strips and a second cross-connector uniting said second and third end portions of said strips, said cross-connectors forming the sole connections between said strips in the region of said first, second, third and fourth end portions of the strips.

8. A resilient frame in accordance with claim 7, further including a medial portion bearing said arms and wherein each of said arms includes first, second, third and fourth strips and first and second cross-connectors all as aforesaid.

9. A resilient frame in accordance with claim 8, wherein said first and third strips extend from said end portions of the frame and are appreciably longer than said second and fourth strips for enabling the space between the opposed strips to remain virtually constant despite the greater stress inherently imposed on said second and fourth strips than on said first and third strips when the end portions of the arms are pulled farther apart than in the unstressed condition of the frame.

10. A resilient frame in accordance with claim 7 wherein one of said arms is formed largely of said first and third strips and the other of said arms is formed largely of said second and fourth strips.

11. An acoustic headset including a pair of earpieces, acoustic tubes having respective ends bearing said earpieces, and a resilient frame constraining lengths of said tubes extending to said respective ends thereof for directing and biasing said earpieces toward the ear canals of a wearer, said frame having resilient serially arranged inner strips and resilient serially arranged outer strips spaced from and opposed to said inner strips, respectively, so as to constitute a first pair of opposed strips and a second pair of opposed strips forming guides for said tubes, said inner strips having respective end portions close to each other and said outer strips having respective end portions close to each other, a cross-connector uniting said end portion of the inner strip of said first pair of strips to said end portion of the outer strip of said second pair of strips, and a second cross-connector uniting said end portion of the outer strip of said first pair of said strips to said end portion of the inner strip of said second pair of strips.

12. A resilient frame having end portions connected to resilient arms spaced apart and arranged to support earpieces of an acoustic headset and to bias earpieces of the headset toward the ears of a wearer, said arms being formed largely of inner and outer pairs of opposed strips, the opposed strips being spaced apart for receiving acoustic tubes therebetween, said inner strips being disposed closer to a centerline between the spaced-apart arms than said outer strips, said strips including first and second inner strips disposed in series and having respective first and second end portions adjacent each other and said strips including third and fourth outer strips disposed in series and opposed to said first and second strips, respectively, and having respective third and fourth end portions adjacent each other, a first cross-connector uniting said first and fourth end portions of said strips and a second cross-connector uniting said second and third end portions of said strips, said cross-connectors forming the sole connections between said strips in the region of said first, second, third and fourth end portions of the strips.

* * * * *